(12) United States Patent
Papp (10) Patent No.: US 10,111,767 B2
(45) Date of Patent: Oct. 30, 2018

(54) SHEATHS USED IN POLYMER SCAFFOLD DELIVERY SYSTEMS

(75) Inventor: John E. Papp, Temecula, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 1552 days.

(21) Appl. No.: 12/916,349

(22) Filed: Oct. 29, 2010

(65) Prior Publication Data

US 2012/0109281 A1    May 3, 2012

(51) Int. Cl.
| | |
|---|---|
| *A61F 2/958* | (2013.01) |
| *A61F 2/97* | (2013.01) |
| *B29C 63/42* | (2006.01) |
| *B29C 61/06* | (2006.01) |
| *A61F 2/966* | (2013.01) |
| *B29C 65/56* | (2006.01) |
| *B29C 65/68* | (2006.01) |
| *B29C 65/00* | (2006.01) |
| *B29L 28/00* | (2006.01) |
| *B29L 31/00* | (2006.01) |
| *B29C 47/00* | (2006.01) |

(52) U.S. Cl.
CPC ............... *A61F 2/958* (2013.01); *A61F 2/97* (2013.01); *B29C 63/42* (2013.01); *A61F 2002/9583* (2013.01); *A61F 2002/9665* (2013.01); *B29C 47/0023* (2013.01); *B29C 61/065* (2013.01); *B29C 65/56* (2013.01); *B29C 65/68* (2013.01); *B29C 66/532* (2013.01); *B29C 2793/0081* (2013.01); *B29L 2028/00* (2013.01); *B29L 2031/7543* (2013.01); *Y10T 29/49863* (2015.01)

(58) Field of Classification Search
USPC ............... 623/1.12, 1.23, 13.15; 604/103.05
See application file for complete search history.

(56) References Cited

U.S. PATENT DOCUMENTS

| | | |
|---|---|---|
| 4,243,050 A | 1/1981 | Littleford |
| 4,581,025 A | 4/1986 | Sheath |
| 4,710,181 A | 12/1987 | Fuqua |
| 4,846,811 A | 7/1989 | Vanderhoof |
| 5,158,545 A | 10/1992 | Trudell et al. |
| 5,211,654 A | 5/1993 | Kaltenbach |
| 5,250,033 A | 10/1993 | Evans et al. |
| 5,352,236 A | 10/1994 | Jung et al. |
| 5,386,817 A | 2/1995 | Jones |
| 5,458,615 A | 10/1995 | Klemm et al. |
| 5,545,211 A | 8/1996 | An et al. |
| 5,591,226 A | 1/1997 | Trerotola et al. |
| 5,643,175 A | 7/1997 | Adair |
| 5,647,857 A | 7/1997 | Anderson et al. |
| 5,653,697 A | 8/1997 | Quiachon et al. |
| 5,693,066 A | 12/1997 | Rupp et al. |
| 5,709,703 A | 1/1998 | Lukic et al. |

(Continued)

OTHER PUBLICATIONS

U.S. Appl. No. 12/831,878, filed Jul. 7, 2010, Van Sciver.
U.S. Appl. No. 12/861,719, filed Aug. 23, 2010, Wang et al.

*Primary Examiner* — Leslie Lopez
(74) *Attorney, Agent, or Firm* — Squire Patton Boggs (US) LLP (57) ABSTRACT

A medical device includes a polymer scaffold crimped to a catheter having an expansion balloon. A sheath is placed over the crimped scaffold after crimping to reduce recoil of the crimped polymer scaffold. The sheath is removed before the medical device is implanted within the body.

11 Claims, 7 Drawing Sheets

(56) References Cited

U.S. PATENT DOCUMENTS

| | | | |
|---|---|---|---|
| 5,749,852 A | 5/1998 | Schwab et al. | |
| 5,765,682 A | 6/1998 | Bley et al. | |
| 5,776,141 A | 7/1998 | Klein et al. | |
| 5,782,855 A | 7/1998 | Lau et al. | |
| 5,800,517 A * | 9/1998 | Anderson et al. | 623/1.11 |
| 5,817,100 A | 10/1998 | Igaki | |
| 5,868,707 A * | 2/1999 | Williams et al. | 604/103 |
| 5,893,868 A | 4/1999 | Holman et al. | |
| 5,964,730 A | 10/1999 | Williams et al. | |
| 5,992,000 A * | 11/1999 | Humphrey | A61F 2/958 29/282 |
| 6,010,529 A | 1/2000 | Herweck et al. | |
| 6,013,854 A * | 1/2000 | Moriuchi | A61F 2/91 606/194 |
| 6,110,146 A | 8/2000 | Berthiaume et al. | |
| 6,132,450 A | 10/2000 | Hanson et al. | |
| 6,152,944 A | 11/2000 | Holman et al. | |
| 6,197,016 B1 | 3/2001 | Fourkas et al. | |
| 6,254,609 B1 | 7/2001 | Vrba et al. | |
| 6,334,867 B1 | 1/2002 | Anson | |
| 6,342,066 B1 | 1/2002 | Toro et al. | |
| 6,355,013 B1 | 3/2002 | Van Muiden | |
| 6,416,529 B1 | 7/2002 | Holman et al. | |
| 6,533,806 B1 | 3/2003 | Sullivan et al. | |
| 6,783,542 B2 | 8/2004 | Eidenschink | |
| 6,790,224 B2 | 9/2004 | Gerberding | |
| 6,805,703 B2 | 10/2004 | McMorrow | |
| 6,827,731 B2 | 12/2004 | Armstrong et al. | |
| 6,899,727 B2 | 5/2005 | Armstrong et al. | |
| 7,198,636 B2 | 4/2007 | Cully et al. | |
| 7,314,481 B2 | 1/2008 | Karpiel | |
| 7,347,868 B2 | 3/2008 | Burnett et al. | |
| 7,384,426 B2 | 6/2008 | Wallace et al. | |
| 7,618,398 B2 | 11/2009 | Holman et al. | |
| 2001/0004735 A1 | 6/2001 | Kindo et al. | |
| 2002/0052640 A1 | 5/2002 | Bigus et al. | |
| 2002/0099431 A1* | 7/2002 | Armstrong | A61F 2/95 623/1.11 |
| 2003/0004561 A1 | 1/2003 | Bigus et al. | |
| 2003/0055481 A1* | 3/2003 | McMorrow | A61F 2/95 623/1.11 |
| 2003/0212373 A1 | 11/2003 | Hall et al. | |
| 2004/0073286 A1 | 4/2004 | Amstrong et al. | |
| 2004/0098118 A1* | 5/2004 | Granada | A61F 2/91 623/1.42 |
| 2004/0133261 A1 | 7/2004 | Bigus et al. | |
| 2004/0143315 A1 | 7/2004 | Bruunn et al. | |
| 2006/0015135 A1 | 1/2006 | Vrba et al. | |
| 2006/0015171 A1 | 1/2006 | Armstrong et al. | |
| 2006/0036310 A1* | 2/2006 | Spencer et al. | 623/1.12 |
| 2007/0061001 A1* | 3/2007 | Durcan | A61F 2/958 623/1.12 |
| 2007/0208408 A1 | 9/2007 | Weber et al. | |
| 2009/0254169 A1 | 10/2009 | Spenser et al. | |

* cited by examiner

SHEATHS USED IN POLYMER SCAFFOLD DELIVERY SYSTEMS

BACKGROUND OF THE INVENTION

Field of the Invention

The present invention relates to drug-eluting medical devices; more particularly, the invention relates to sheaths for polymeric scaffolds crimped to a delivery balloon.

Background of the Invention

A variety of non-surgical interventional procedures have been developed over the years for opening stenosed or occluded blood vessels in a patient caused by the build up of plaque or other substances on the walls of the blood vessel. Such procedures usually involve the percutaneous introduction of an interventional device into the lumen of the artery. In one procedure the stenosis can be treated by placing an expandable interventional device such as an expandable stent into the stenosed region to hold open and sometimes expand the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a metal or metal alloy structure, generally speaking, while a scaffold will refer to a polymer structure. It is understood, however, that the art sometimes uses the term "stent" when referring to either a metal or polymer structure.

Metal stents have traditionally fallen into two general categories—balloon expanded and self-expanding. The later type expands to a deployed or expanded state within a vessel when a radial restraint is removed, while the former relies on an externally-applied force to configure it from a crimped or stowed state to the deployed or expanded state.

For example, self-expanding stents formed from, for example, shape memory metals or super-elastic nickel-titanum (NiTi) alloys are designed to automatically expand from a compressed state when the stent is advanced out of a distal end of the delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired examples. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be disposed within a sheath, either during a transluminal delivery to a target site or during the assembly of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating such as when the blades and/or stent struts are misaligned during the diameter reduction. Examples of stents that utilize a sheath to protect the stent during a crimping process are found in U.S. Pat. Nos. 6,783,542 and 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 2010/0004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a delivery system having a polymer scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bio-absorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bioabsorbable polymer such as PLLA or PLGA. Challenges faced when securing a polymer scaffold to a delivery balloon are discussed in US20120042501.

In view of the foregoing, there is a need to address the unique challenges associated with securing a polymer scaffold to a delivery balloon and maintaining the integrity of a scaffold-balloon catheter delivery system up until the time when the scaffold and balloon are delivered to a target site within a body.

SUMMARY OF THE INVENTION

The invention is directed to sheaths used to maintain a polymer scaffold—balloon engagement and delivery system profile and methods for assembly of a medical device including a balloon expandable polymer scaffold contained within a sheath. The invention is also directed to a sheath and methods for applying a sheath that enable the sheath to be easily removed by a medical professional, e.g., a doctor, without disrupting the crimped scaffold-balloon engagement or damaging the scaffold.

The inventor realized that the effect on production when using a polymer, e.g., PLLA, as opposed to a metal for a balloon-expanded medical device is significant. When using a polymer, several of the accepted processes for the metal structure, e.g., crimping, sterilization and the packaging of the metal stent up until the time when the device is implanted within a body will likely need significant modification in order to properly accommodate the special requirements of a balloon-expanded polymer. In one sense, processing steps including crimping, sterilization and packaging for a polymer scaffold are generally more involved and time consuming than for a metal stent.

Compared to a polymer scaffold, a metal stent may be crimped to a balloon at relatively high temperatures and radial forces since the material is more ductile and less sensitive to crimping deformation affecting its deployed radial strength. Stated somewhat differently, metal materials used for stents are generally capable of being worked more during the crimping process than polymer materials. This desirable property of the metal allows for higher dislodgment forces and less concern over the metal stent-balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly may not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site.

In contrast, greater care may be needed during crimping and the subsequent packaging for a polymer scaffold-balloon catheter delivery system. For instance, when a relatively brittle material such as PLLA is used, it may be necessary to perform the diameter reduction during crimping within a restricted temperature, application rate and applied force range so that the scaffold will exhibit the desired deployed radial strength and not suffer from excessive cracking or fracture when later deployed by the balloon. In one example, the deployed radial strength may be enhanced by forming the scaffold at, or near to its deployed diameter. This method of fabrication can produce a scaffold possessing a shape memory corresponding to the deployed state; hence, a scaffold having improved radial strength. Examples of this scaffold type are discussed in US20100004735.

As explained earlier, the desirable properties of a metal stent allows it to be worked during the crimping process to significantly reduce, if not eliminate any appreciable recoil. As a result, there is generally no treatment, processing or packaging needed to address recoil in the material. The inventor has realized that the same is not true for a scaffold. While the scaffold may be formed so that it is capable of being crimped in such a manner as to reduce inherent elastic recoil tendencies in the material, e.g., by maintaining crimping blades on the scaffold surface for an appreciable dwell period, the methods employed during crimping of the polymer material are limited. Significantly, the material generally is incapable of being worked to the degree that a metal stent may be worked without introducing deployed strength problems, such as excessive cracking in the material. As a consequence, a sheath is needed to prevent the polymer scaffold from elastically recoiling to a larger diameter after being removed from the crimping mechanism.

In a preferred embodiment, a sheath is used to maintain scaffold-balloon engagement and desired delivery profile following a crimping process for a scaffold formed at a diameter near to its deployed diameter. As noted earlier, a scaffold formed at its deployed diameter can exhibit enhanced radial strength over a scaffold formed nearer to its crimped diameter, which is often the diameter chosen for a metal stent. The enhanced radial strength properties for a scaffold formed near to its deployed diameter, however, also increases the propensity for elastic recoil in the scaffold following a crimping process. Hence, the shape memory desirable for enhancing radial strength at deployment can also introduce greater elastic recoil problems after the scaffold is crimped to the balloon. In one aspect, the invention is directed towards solving this problem.

In another aspect, the invention is directed to a sheath and methods for applying the sheath to a crimped scaffold that may be removed by a medical specialist such as a doctor without risk of the scaffold becoming dislodged from the balloon when the scaffold is removed by the medical specialist. The sheath is preferably removed from the crimped scaffold before the scaffold is inserted into the body. In this aspect of the invention a sheath is provided that both reduces recoil problems and is easily removed by a medical specialist without dislodging the scaffold from the balloon to which it is crimped.

In one aspect of the invention there is a method for crimping. The method includes the steps of providing a polymer scaffold having a first diameter (d1), providing a balloon catheter, and crimping the scaffold to the balloon catheter including the step of reducing the scaffold diameter from the first diameter to a second diameter (d2) wherein the ratio of d1/d2 is at least about two. The method further includes the step of reducing recoil effects in the crimped scaffold including deforming a sheath to enable the sheath to be received over the crimped scaffold, and after being received over the crimped scaffold, allowing the sheath to return to an un-deformed state.

The method is useful to reduce recoil concerns following a large diameter reduction during crimping for a polymer material. The method is particularly useful for ratios d1/d2 greater than about 3:1 or between about 3:1 to 6:1. The sheath may have an un-deformed inner diameter that is less than d2 when the sheath has a temperature corresponding to the storage temperature of the packaged medical device. The sheath may be placed on the scaffold at a first temperature. Then, when packaged and awaiting use at the storage temperature, the sheath will shrink to its un-deformed size to impart an inwardly directed radial preload on the crimped scaffold. The storage temperature may be lower than the first temperature.

In another aspect of the invention there is an apparatus including a medical device for being implanted within a body. The apparatus includes a polymer scaffold crimped to a delivery balloon and a sheath disposed over the crimped scaffold, the sheath being constructed so as to apply a radial preload to the scaffold to reduce recoil in the scaffold when attached to the scaffold. The sheath is also configured for being manually removed before a medical procedure.

The medical device may include a non-compliant delivery balloon having a maximum inflated outer diameter d3, the scaffold has a crimped inner diameter d2 and the scaffold is cut from an expanded tube having an inner diameter d1, wherein d1/d2 is greater than 6:1. In a further aspect the medical device may have a scaffold and crimped diameter such that d3 is less than d1.

In another aspect of invention, there is a method for providing a medical device suitable for implantation within a body. The steps include crimping a polymer scaffold to a balloon catheter and disposing a sheath over the crimped scaffold to reduce recoil in the crimped scaffold. This disposing step corresponds to only one of (a) and (b): (a) radially expanding the warmed sheath at a first temperature, and then disposing the radially expanded sheath over the crimped scaffold to apply a radial pre-load to the scaffold, the sheath including a removal portion and then storing the medical device at a storage temperature below the first temperature, and (b) providing a sheath having a plurality of tabs to enable manual attachment and removal of the sheath from the scaffold using the plurality of tabs. When the sheath is manually removed using the removal portion or tabs, respectively, the crimped scaffold and balloon catheter then become suitable for implantation within a body.

In another aspect of invention a sheath is heat set to curl or naturally form a cylinder with ends that may be used as pull tabs to apply and remove the sheath to the crimped scaffold without the use of a fastening tape.

In another aspect of invention, a sheath is formed from a radially deformed tube having a diameter greater than the crimped scaffold diameter. After this radially deformed sheath is placed over the scaffold, heat is applied to cause the sheath to shrink to the undeformed diameter of the tube from which the sheath was formed.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

A polymer scaffold according to a preferred embodiment is formed from a radially expanded, or biaxially expanded extruded PLLA tube. The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimper is used to crimp the scaffold to the balloon. The desired crimped profile for the scaffold is ½ or less than ½ of the starting (pre crimp) diameter of the expanded tube and scaffold. In the embodiments the ratio of the starting diameter (before crimping) to the final crimp diameter may be 2:1, 2.5:1, 3:1, or higher. For example, the ratio of starting diameter to final crimped diameter may be greater than the ratio of the deployed diameter to the final crimped diameter of the scaffold, e.g., from about 4:1 to 6:1.

In one embodiment, a scaffold-balloon catheter assembly may have about a 8 mm initial scaffold diameter (or expanded tube diameter) that is crimped to about a 2 mm crimped diameter on a 6.5 mm diameter non-compliant balloon. When deployed, the scaffold according to this embodiment would have about a 6.5 mm deployed diameter (less than the tube's diameter of 8 mm). Thus, in this example the ratio of starting diameter to crimped diameter is 4:1. In another example, the expanded tube diameter is 8 mm and the scaffold is crimped down to a 2.5 mm diameter. In still another example, the expanded tube diameter is 12 mm and the crimped diameter is 2.5 mm. In each case the scaffold may be crimped to a 6.5 mm balloon.

The memory of the scaffold material following crimping will induce some recoil when the scaffold is removed from the crimper. While a dwell period within the crimper can reduce this recoil tendency, it is found that there is residual recoil that can be restrained by selecting an appropriately sized sheath over the crimped scaffold. This need to reduce recoil is particularly evident when the diameter reduction during crimping is high, since for a larger starting diameter compared to the crimped diameter the crimped material can have higher recoil tendencies.

Figure 1:
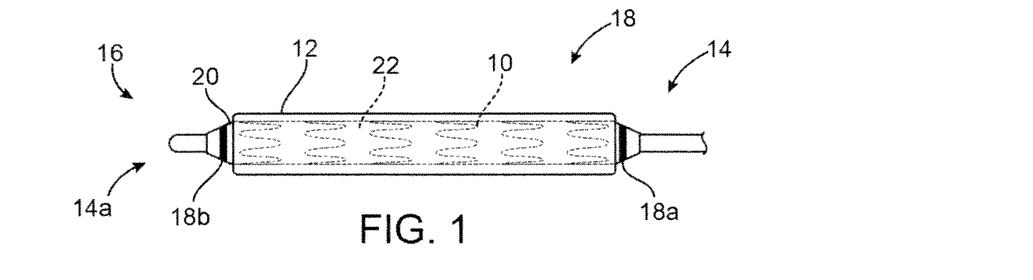
FIG. 1 is a side view of a polymer scaffold-balloon catheter assembly (medical device) with a sheath placed over the crimped scaffold.

FIG. 1 is a side view of a scaffold-balloon catheter assembly 18 ("medical device 18"). A polymer scaffold 10, e.g., a scaffold having 2.5:1 or higher diameter reduction during crimping, is crimped to a balloon 20 of the catheter. A sheath 12 is disposed over the crimped scaffold 10 and balloon 20. The scaffold is located between distal and proximal balloon markers 18a, 18b. The balloon catheter has a distal portion 16 and proximal portion 14. The shaft of the catheter has an inner lumen for a guidewire. The scaffold 10 and balloon 20 are engaged with each other such that portions of the balloon material extend at least partially between struts of the scaffold 10. It is desirable that this engagement between scaffold 10 and balloon 20 is maintained by the sheath 12 so as to retain the dislodgment force formed during crimping. "Dislodgment force" refers to the threshold force applied longitudinally over the surface of the scaffold 10 that will dislodge the scaffold 10 from the balloon 20. In one embodiment the dislodgment force is between 1 and 2 pounds. As compared to metal stents, the dislodgment force of a polymer scaffold can be noticeably less, particularly when the scaffold is subjected to a large diameter reduction during crimping.

The sheath may be made from Pebax, PTFE, Polyethelene, Polycarbonate, or Nylon. Polyimide may also be used. This material is very dimensionally stable and will not creep over time. Polyimide also rips more easily once a tear has been started. Polymide may therefore be preferred for a sheath designed to have weakened areas along the length of the sheath to direct tear propagation when removing the sheath.

The sheath 12 also serves to maintain the crimped diameter of the crimped scaffold 10 at a crossing profile or profile, i.e., diameter, suited for delivery to the target vessel within the body for performing the medical procedure, e.g., percutaneous transluminal angioplasty (PTA). This diameter may correspond to about the final crimp diameter for the scaffold 10. The sheath 12 size is chosen so that, when initially disposed over the scaffold, the sheath 12 applies a net inwardly directed radial force on the scaffold 10 to resist any recoil tendencies in the scaffold 10 following the crimping process and to maintain the scaffold-balloon dislodgment force formed during the crimping process. Preferably the sheath 12 is disposed over the scaffold 10 and balloon 20 immediately following crimping.

The method used to apply the sheath 12 to the scaffold 10 should be chosen so that there is no tendency for the scaffold 10 to be shifted or dislodged from the balloon 20 as the sheath 12 is being applied. This need may become evident when only a comparatively low dislodgment force (as compared to a metal stent) may be achievable for the scaffold-balloon catheter assembly. Moreover, or in addition there may be a need to avoid creep that can occur in the folded balloon material. By applying a preload through a properly fitted sheath, dimensional changes in both the balloon material and scaffold (effecting the crossing profile and/or dislodgment force) can be minimized during the storage period when the medical device is awaiting use. To this end, two possible embodiments of a sheath application process are contemplated and illustrated in FIGS. 3A-3B and 4A-4B. In each of these processes, the sheath 12 is stretched using a mandrel or collets so that its inner diameter is large enough to allow the crimped scaffold 10 and balloon 20 to be easily placed within the bore of the sheath 12 without risk of scaffold dislodgment due to surface-to-surface contact between the scaffold 10 and the sheath 12 bore. The sheath 12 may also be warmed to increase its inner diameter relative to the scaffold 10 crimped diameter when the scaffold 10 is placed within the sheath 12. After the scaffold 10 is positioned within the sheath 12 bore the sheath 12 is allowed to return to its initial, un-stretched diameter. The sheath 12 may have an un-stretched or un-deformed diameter at a first temperature, such as a storage temperature, less than the crimped diameter of the scaffold. As such, the sheath 12 in these embodiments can be selected to impose a net inward force on the scaffold 10 to counter any recoil tendencies in the polymer material when the balloon-scaffold and sheath are packaged and awaiting use at about the first temperature, e.g., room temperature or below room temperature. The higher temperature for placing the sheath should be selected to avoid negative effects on the polymer scaffold, balloon or coating due to heat. For a PLLA scaffold, for example, it has been found acceptable to have the scaffold exposed for a period of between ½ hour to one hour at temperatures of about 80 degrees Celsius. For shorter periods of exposure higher temperatures may be used. In the embodiments for materials such as PLLA and PLGA a temperature of between about 80-100 degrees Celsius or higher may be used to effect expansion of appropriately chosen sheath material (as disclosed herein) risking adverse effects on the scaffold.

Figure 2:
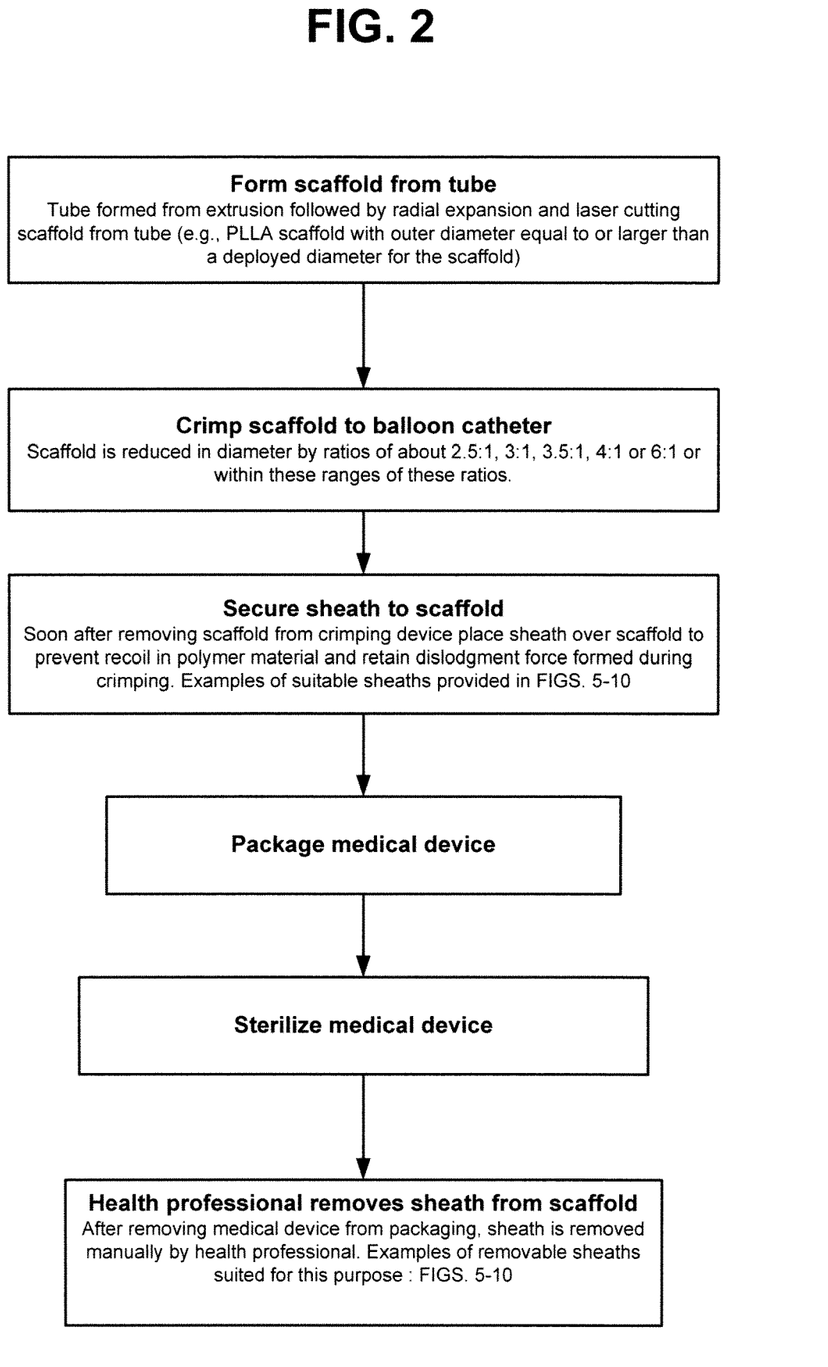
FIG. 2 is a flowchart showing steps involved in the fabrication of the scaffold and assembly of the medical device of FIG. 1, and the post-crimping processing and preparation of the medical device for implantation according to one aspect of the disclosure.

Referring to FIG. 2, a flowchart summarizes the steps involved in the production and packaging of the medical device and preparation of the medical device before being implanted within a body. The steps include forming the expanded tube, forming the scaffold from the expanded tube by cutting the scaffold 10 from the tube using a laser, crimping the scaffold to a balloon catheter, attaching the sheath 12 to the crimped scaffold 10 and balloon 20 portion of the medical device, placing the medical device within a package, and sterilizing the medical device package. The scaffold fabrication and crimping aspects of the process are described in U.S. patent application Ser. Nos. 12/861,719 and 12/831,878. Before implanting within a patient, the sheath 12 may be removed from the scaffold. Embodiments of such a manually removable sheath are discussed in greater detail, below.

Figure 3A:
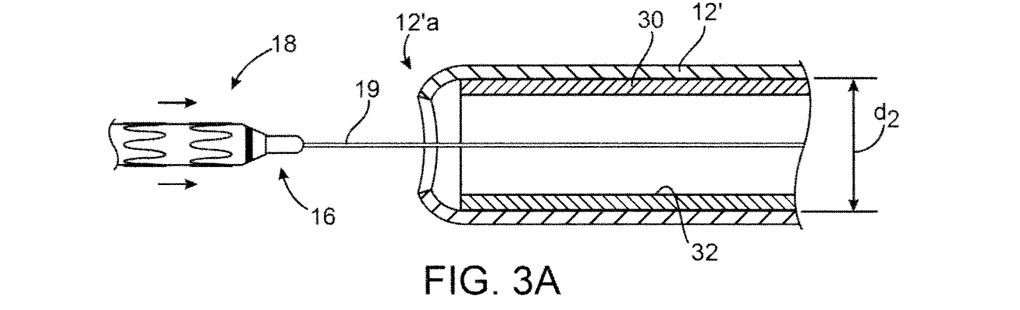
FIGS. 3A-3B are side views showing one embodiment for applying a sheath to the crimped scaffold portion of the medical device of FIG. 1.
Figure 3B:
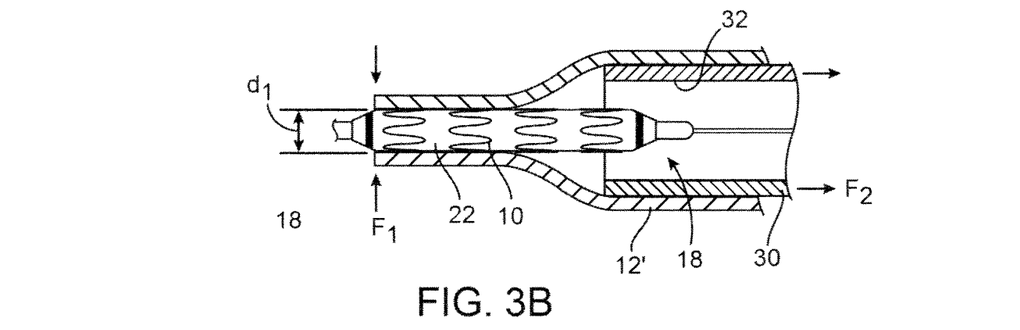
Figure 4:
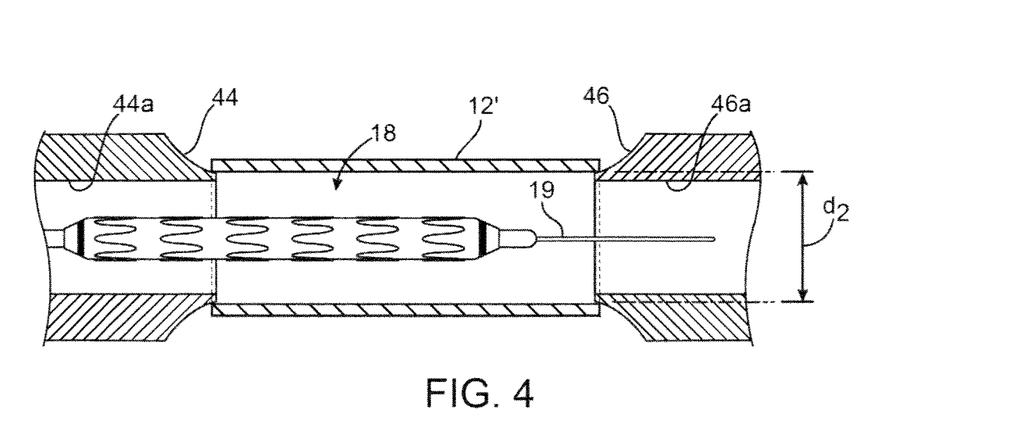
FIG. 4 is a side view showing another embodiment for applying a sheath to the crimped scaffold portion of the medical device of FIG. 1.

Referring to FIGS. 3A-3B, in one embodiment the sheath 12 is forcibly placed over a hollow tube 30 so that its inner diameter d1 is stretched to a diameter d2 as illustrated. The bore 32 of tube 30 is sized so that the assembled medical device 18 can easily pass through the tube bore 32. A guidewire 19 may be used to direct the medical device 18 through the bore 32. With the scaffold disposed within the bore 32, the sheath end is then held in place (as indicated by F1) and the tube withdrawn as shown in FIG. 3B. As the deformed sheath 12' separates from the tube 30 it returns to its un-deformed state and attaches to the surface of the scaffold 10. Since the sheath has an initial, un-deformed diameter d1 less than the crimped scaffold diameter 10 the sheath 12' when separated from the tube 30 and attached to the scaffold 10 imposes a net radial inward force on the scaffold 10, thereby resisting outward recoil of the scaffold 10. The sheath 12 may be warmed before being stretched over the tube 30, then allowed to cool after being attached to the scaffold 10, e.g., return to room temperature.

Another method for securing the sheath 12 to the scaffold is described with the aid of FIG. 4. In this embodiment, the sheath 12 is radially expanded and held in this deformed state by being supported upon opposed collets 46, 44, each of which have an inner bore 44a, 46a for passage of the guidewire 19 and medical device 18 within the deformed sheath 12'. With the scaffold and balloon disposed within the space 40 the collets 44, 46 are then moved apart so that the sheath 12' is allowed to return to its un-stretched diameter d1. The sheath 12' may be maintained at a warmer temperature when held between the collets 46, 44 then allowed to return to a cooler temperature once attached to the scaffold 10, as before.

In another rembodiment a pre-stretched sheath may be placed over a crimped scaffold then heat applied which causes the sheath to shrink in size. The sheath may be made from a suitably chosen polymer, e.g., among those listed in this disclosure. The sheath may be formed from an extruded tube that is radially expanded. The expanded (radially deformed) tube preferably has an inside diameter that is larger than the scaffold crimped diameter or crossing profile. The sheath is cut from the tube. The scaffold may then be placed within the radially deformed sheath and heat applied to shrink the tube back to its starting, or un-deformed diameter. To increase or decrease the applied preload on the scaffold the tube thickness may be increased or decreased, respectively.

According to another aspect of the disclosure, a sheath for a crimped polymer scaffold is formed so that it may be easily removed by a medical professional, e.g., a doctor, before performing the medical procedure. According to a first aspect of this disclosure, various slits, cuts or weakened areas may be pre-formed in the sheath to facilitate a tearing away or removal of the sheath from the scaffold 10 without dislodging the scaffold 10 from the balloon 20. That is, the sheath is formed so that when a medical professional applies a pulling or tearing force to the sheath the movement of the sheath will not also tend to pull the scaffold 10 from the balloon 20, thereby dislodging the scaffold 10 from the balloon 20. The removable sheath having weakened areas is preferably designed so that it can be easily removed without applying an excessive pulling force on the medical device 18. That is, the manner of removal is such that the forces applied to the scaffold 10 impose the least amount of longitudinally directed forces over the surface of the scaffold 10. Longitudinally directed forces over the surface of the scaffold 10 refer to forces that tend to dislodge the scaffold 10 from the balloon 20, as in the case when the scaffold is passed through the body.

The embodiments of removable sheaths having weakened areas are particularly suitable for sheaths that are heated to expand when placing over the sheath and the embodiment of a radially deformed sheath that is heated to shrink down upon the scaffold. Thus, the following discussion in connection with FIGS. 5-7 is understood to apply to either sheath type.

Additionally, is contemplated that the methods employed to form the weakened areas may form the weakened areas before or after the sheath is applied. Thus, according to some embodiments a uniform sheath is applied, e.g., by applying heat, then v-cuts, holes, cuts, etc. are formed either before or after the sheath is disposed over the crimped scaffold.

In view of these objectives, it will be appreciated that a sheath having weakened areas according to the disclosure may be formed for removal in a different manner than, e.g., a weakened sheath intended for removal when the balloon is expanded. In the case of sheaths designed for removal when a balloon is expanded, the sheath is implanted within the medical device, as opposed to being removed before the medical device is implanted within the body. When the stent reaches its target, the balloon is then expanded. The weakened areas in the sheath are formed so that the sheath fails when radial outward forces are applied by the balloon. Examples of these implanted sheath types are shown in US 2004/0073286.

Figure 5A:
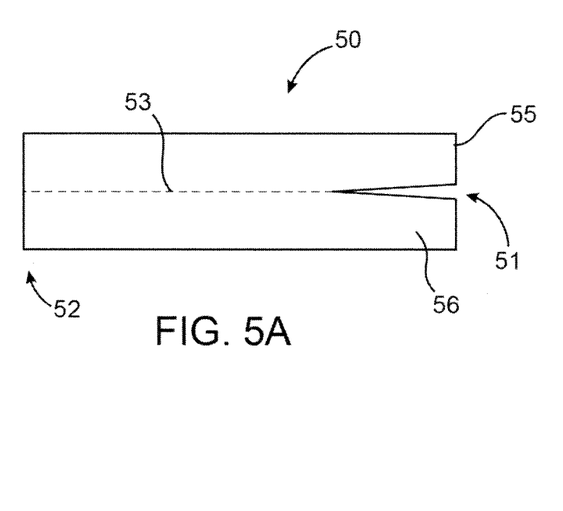
FIGS. 5A-5B illustrate aspects of a removable sheath according to a first embodiment.
Figures 5B, 6B:
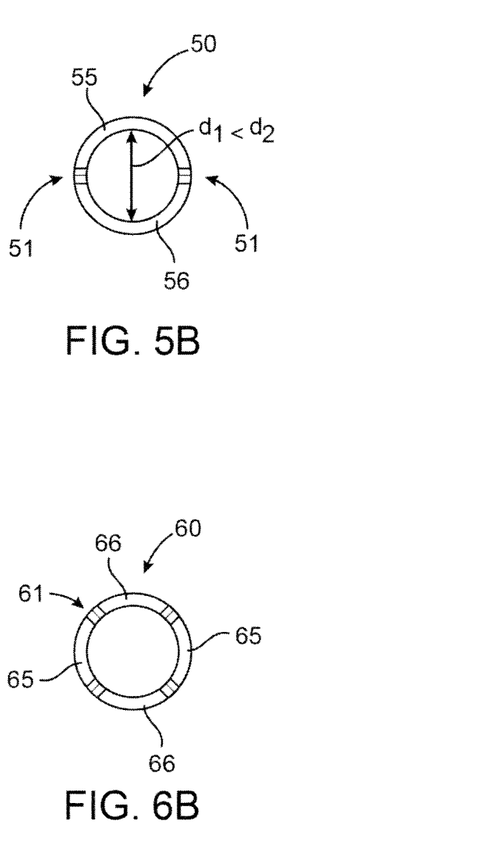
FIGS. 6A-6B illustrate aspects of a removable sheath according to a second embodiment.
Figure 6A:
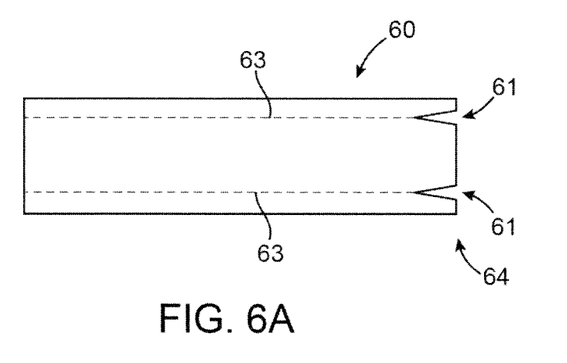
Figure 7:
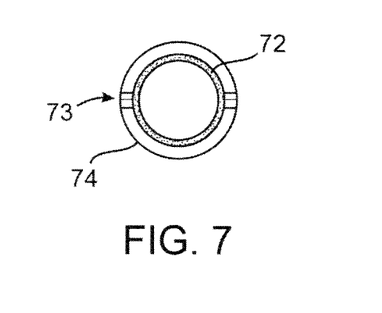
FIG. 7 illustrates aspects of a removable sheath according to a third embodiment.

FIGS. 5-7 show aspects of sheaths 50, 60 and 70 according to first, second, third and fourth aspects, respectively, of the removable sheath disclosure. The methods described in connection with FIGS. 3-4 may be utilized to apply sheaths 50, 60, 70 to a scaffold. Moreover, it will be appreciated that features of the embodiments of the sheaths 50, 60 and 70 may be combined. For example, the features of sheath 60 may be combined with of sheath 70 to produce a sheath that has multiple layers and multiple v-cuts to facilitate a sheath that may be both readily attached and removed from a crimped scaffold without disturbing its engagement or placement on the delivery balloon.

Referring to FIGS. 5A-5B, a sheath 50 includes weakened areas 51 and 53 arranged so that a medical professional may remove the sheath by tearing the sheath manually along lines of weaknesses in the sheath. When disposed over the scaffold 10 the sheath 50 may have a proximal end 52 and distal end 54 located, respectively, near the proximal and distal balloon markers 18a, 18b (FIG. 1). At the distal end 54 there as a pair of opposed v-shaped cuts defining upper and lower pull flaps 55 and 56. The dashed lines 53 indicate the intended tear line when the opposed flaps 55, 56 are manually pulled apart to initiate tearing along the line 53. In one embodiment, the tear lines 53 may also correspond to pre-formed slits, having a depth about half the sheath 50 wall thickness and over the length of the sheath 50. In one embodiment the sheath 50 distal end 54 may extend beyond the scaffold distal end and balloon and be folded up or over the sheath to make the flaps 55, 56 more easy to grip and pull up and down respectively, so as to avoid longitudinally applied forces on the scaffold surface as the sheath 50 is torn away.

Referring to FIGS. 6A-6B, a sheath 60 has a plurality of slits 63 evenly spaced about the circumference of the sheath, e.g., four slits, each separated by 90 degrees. A corresponding four pull flaps 65, 66 may be formed at the distal end 63. According to this embodiment, the flaps formed at the distal end 64 may be incrementally pulled so that less longitudinal force is applied to the scaffold 10.

A sheath 70 shown in FIG. 7 has multiple layers. The inner layer 72 is formed from a more lubricous, i.e., less friction, surface than outer layer 74, so that upon initiating the tearing away of the sheath the surface-to-surface contact between sheath 70 and scaffold will apply less longitudinal forces to the surface of the scaffold. In other words, the sheath will tend to expand slightly since it is no longer radially restrained and slide over the scaffold rather than grip the surface of the scaffold when the sheath 70 is removed.

Figure 8A:
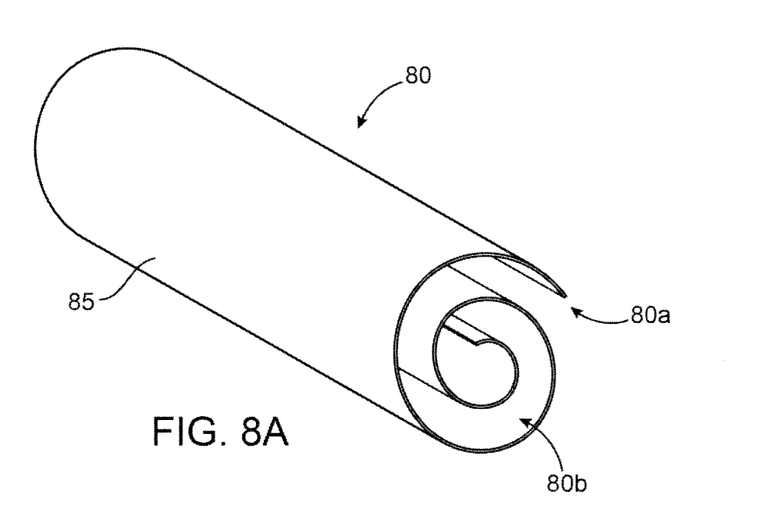
FIGS. 8A-8C illustrate aspects of a removable sheath according to a fourth embodiment.
Figure 8B:
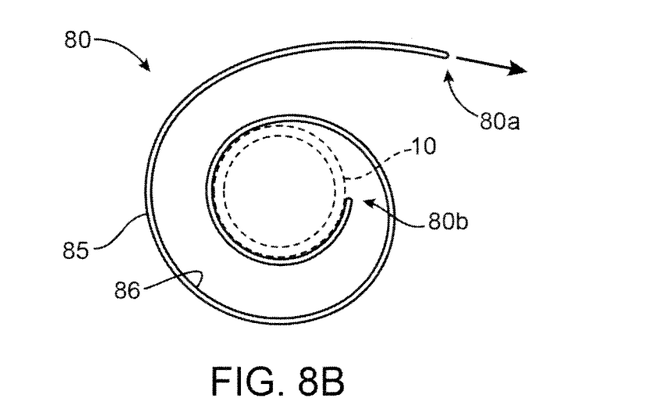
Figure 8C:
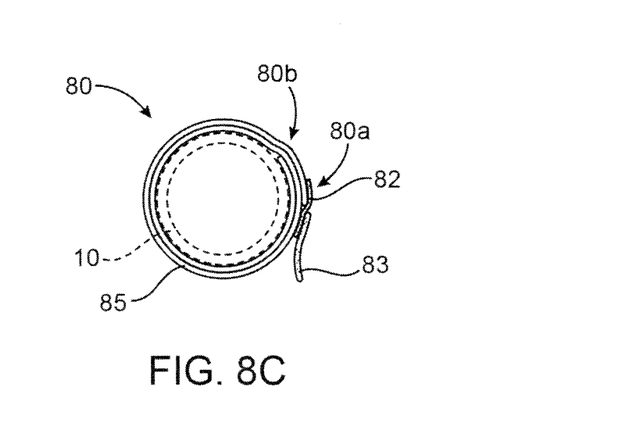

FIGS. 8A-8C show aspects of a sheath 80 according to a fourth aspect of the removable sheath disclosure. Sheath 80 may be generally rectangular in shape, have a length about equal to or greater than the length of the crimped scaffold 10 or the length of the balloon 20. Materials suitable for a sheath of this type include a composite, multi layer polymer sheet or film which can provide a low friction, lubricous side and an elastic outside to facilitate application of a radially inward directed preload on the crimped scaffold to help maintain the crimped diameter and dislodgment force following crimping. For instance, the elastic material may be a thin film stiff material such as "Kapton", which is a Polyimide material that can be heat set into the desired shape and the lubricous material can be Teflon or PTFE. A "Parylene" lubricous coating on one side of elastic material can also be a suitable solution. A preferred solution here would be a Polyimide which was molded with a Polyimide\PTFE blended layer on one side to provide a lubricous surface to contact the scaffold. Sheath 80 may alternatively be made from a single elastic film, which elastic material can be pulled tightly around the crimped scaffold 10.

Sheath 80 is pre-disposed to curl upon its self, as indicated in FIG. 8A. By predisposing the sheath 80 to curl upon itself, attachment of the sheath 80 to the crimped scaffold 10 may be performed more easily; hence avoiding improper attachment to the scaffold 10 than if a flat rectangular sheet were wrapped about the sheath 80. Sheath 80 has an inner side 80*b* and an outer side 80*a*, where inner/outer designations are used to refer to these sides in view of the locations of these sides when the sheath 80 is attached to the scaffold 10.

Referring to FIG. 8B, the distal end of the medical device 18 (scaffold 10 outer diameter in phantom) is placed within the sheath 80 and the sheath 80 allowed to curl up around the scaffold 10. Hence, inner side 80*b* is curled up against the scaffold 10 surface to facilitate wrapping the sheath 80 tightly around the scaffold 10 using outer side 80*b*. The sheath is then wrapped around the scaffold by pulling on the end 80*a* as shown.

Referring to FIG. 8C, here is shown the sheath 80 secured to the scaffold and held in place using a tape 82 having a pull tab 83. To remove the sheath 80 from the scaffold 10, one may pull up on the pull tab 83 using one hand, while the other hand holds the distal tip 16 to prevent excessive torque of the catheter when the tab 83 is pulled upwards.

In alternative embodiments the sheath 80 may have two pull tabs (instead of one) and the sheath may have dimensions that allow it to be wrapped part of a wrap or one or more times around the balloon-scaffold. For example, referring to FIGS. 8D and 8E, sheaths 81 and 88 are depicted. In the case of sheath 88 depicted in FIG. 8E, the folded ends 88*a*, 88*b* serve as pull tabs for unwinding and loosening the sheath from about the scaffold, which then allows the sheath to be easily removed without disturbing the scaffold-balloon engagement. The inner, scaffold-contacting surface of the sheath 88 is surface 87*a* and the outer surface is 87*b*.

Preferably the sheath may be heat set to curl up on itself, as in the case of scaffold 80. The pull tabs could be formed so that they have a more severe fold outward and down further than depicted in FIG. 8E so that they were in contact with or near contact with the outer surface 87*b*. The product may then be packaged and shipped with no need for tape or any other fastening means. In forming the sheath 88 a diameter d3 (FIG. 8E) is selected that is smaller than the crimped scaffold diameter. As such, when fitted to the scaffold the sheath can apply the desired preload and may be easily removed by pulling the ends apart.

Figure 8D:
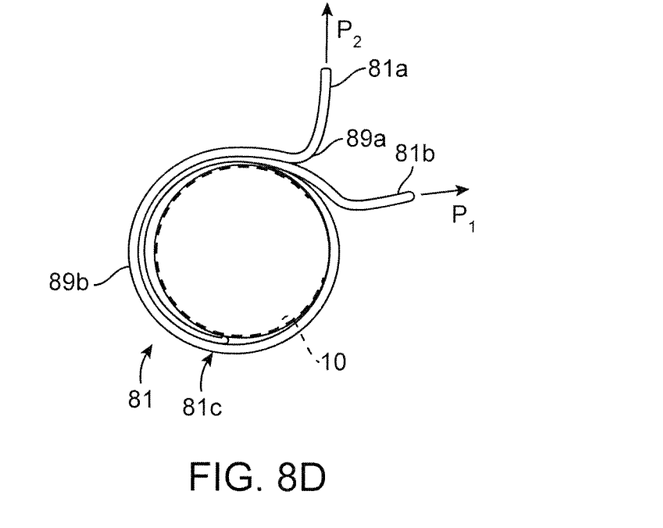
FIGS. 8D-8E illustrate aspects of a removable sheath according to additional aspects of the fourth embodiment.
Figure 8E:
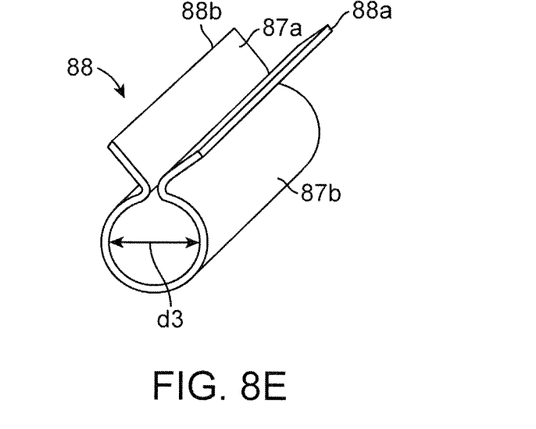

The sheath 81 depicted in FIG. 8D has a circumferential extent that is much greater than the circumference of the crimped scaffold. The inner, sheath contacting surface of the sheath 81 is surface 89*a* and the outer surface is surface 89*b*. In this case, when the sheath is secured to the scaffold the sheath is wrapped about one and one half revolutions around the scaffold. The right tab 81*b* is the end of the sheath 81 that extends out from the folded portion 81*c*. The sheath 81 may be formed to wrap several times around the sheath, twice, three, four or about 1.5 times as depicted in FIG. 8D. The preferred number of wraps may be selected based on the desired pre-load on the scaffold, and the elasticity and/or creep characteristics of the sheath material.

To remove the sheath 81 from the scaffold 10, the tabs 81*a*, 81*b* are pulled in the directions shown as P1, P2. As can be appreciated in light of this disclosure, the sheath may be both tightly or firmly wrapped about the scaffold (to create a desired radial preload) and also released gently due to the sheath's natural tendency to unwrap uniformly about the scaffold circumference as the tabs are pulled in the directions P1, P2. The wrapped sheath arrangement with tabs in FIG. 8E (or 8E) can impart minimal disruption to the scaffold-balloon while still being capable of applying the desired preload since upon pulling the tabs the sheath can essentially pop off the scaffold surface. As in the case of sheath 88 the sheath 81 may be heat set to roll up on itself, which may obviate the need for using a fastening tape.

Figure 10A:
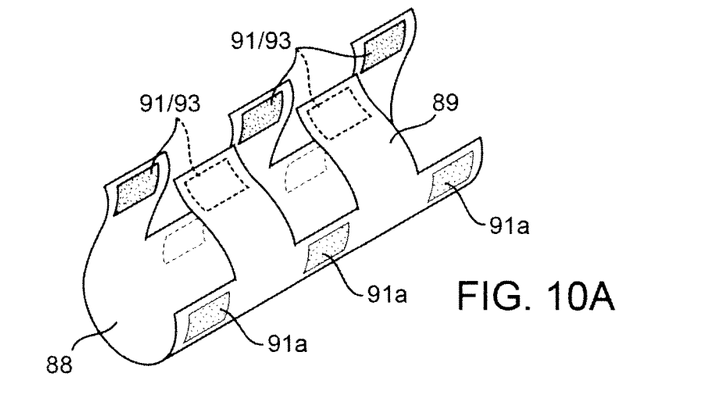
FIGS. 10A-10D illustrate aspects of a removable sheath according to a sixth embodiment.
Figure 10B:
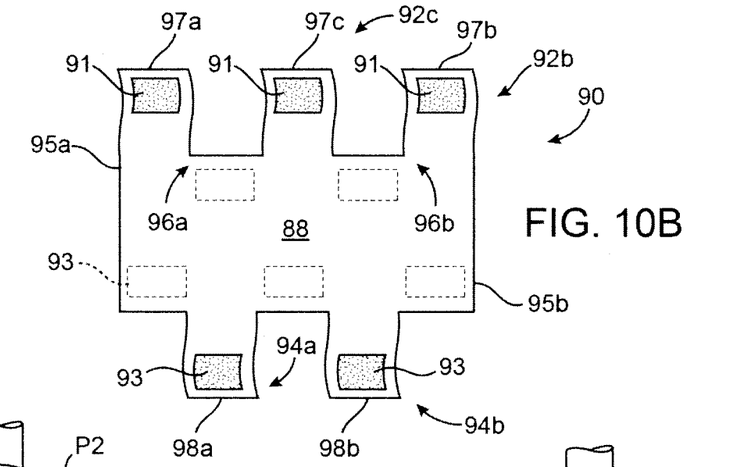
Figure 10C:
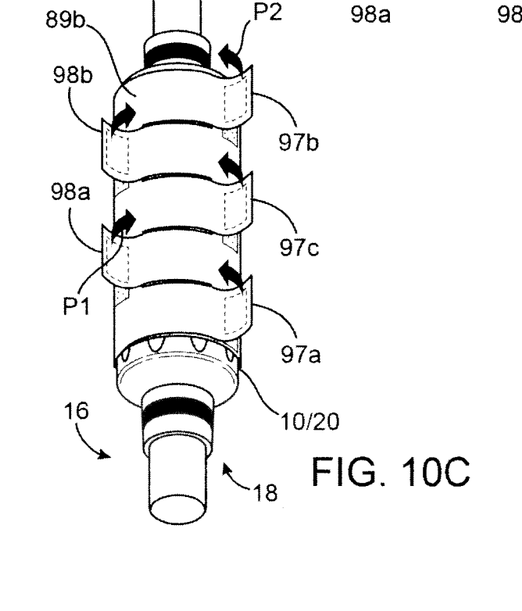

FIGS. 10A-10C show a sheath 90 according to a sixth aspect of the removable sheath disclosure. Sheath 90 is formed from a polymer film cut or formed to be wrapped around the crimped scaffold 10. Materials suitable for a sheath of this type may be the same type as those for sheath 80.

Referring now to FIGS. 10A and 10B there is the sheath 90 having formed on a lower side tabs 94*a* and 94*b* opposing slots 96*a* and 96*b* and tabs 92*a*, 92*b* and 92*c* on an upper side of the sheath 90. Ends 95*a* and 95*b* are separated by a length equal to or greater than the length of the scaffold 10 or balloon 20 (FIG. 1). As indicated in FIG. 10A the distance approximately equal to d1 refers to the extent of the sheath 90 that will extend at least about, if not more than the entire circumference of the crimped scaffold 10 (in a manner similar to the embodiment depicted in FIGS. 8A-8C) to ensure that a uniform and consistent preload may be applied across the entire length of scaffold when the tabs 92, 94 are pulled across each other, i.e., pulled in the direction opposite to P1, P2 in FIG. 10C. To this end, it should be mentioned that over the entire length of the sheath 90 it is preferred that the radial preload applied when tabs 92, 94 are secured are consistent and uniform over the entire length of the sheath 90. Preferably, there are no longitudinal sections that do not have a tab secured via a fastener 91 as this may lead to uneven radial preloading of the scaffold resulting in loss of dislodgment force and/or displacement of the scaffold 10 relative to the balloon 20.

The surface 88 contacts with the surface of the crimped scaffold 10, while the surface 89 is the outer surface of the sheath disposed over the scaffold 10, which outer surface 89 may include both fastening members 91*a* and user indicia or guides 99 as discussed below. The sheet or film from which sheath 90 was formed may be predisposed to curl upon itself in a manner similar to the embodiments depicted in FIGS. 8A-8C, or be a flat sheet not having a bias to curl in the manner shown in FIG. 10A.

Each of the two tabs 94 and three tabs 92 depicted in FIGS. 10A-10C include an inner surface corresponding to a portion of surface 88 and an outer surface corresponding to a portion of outer surface 89. On the inner surface a tab has a first fastening element 91 positioned to mate with a second fastening element 91*a* disposed on the outer surface 89. The fastening element pairs 91, 91*a* are located so that a tab 92, 94 has outboard of fastening element 91 an end 97*a*-97*c* and 98*a*-98*b*, preferably curled or folded upward as shown to facilitate convenient gripping or to indicate to the health professional that these ends should be used to remove the sheath. In one particular embodiment the outer surface portion of end 97, 98 may be colored 99 to serve as an indicia or guide to the person intent on removing the sheath 90 from the scaffold 10 to pull from the end 97, 98 and to pull in a particular manner.

The sheath 90 may be attached to the crimped scaffold in the following manner. First, the scaffold 10 is placed within the half-cylinder section shown in FIG. 10A. Then the tabs 94a, 94b are secured to the outer surface 89 by mating the fasteners 91, 91a associated with a tab 94. The process may include gripping with one hand the tab 92 to hold the sheath 90 in place relative to the scaffold 10 while the tabs 94 are pulled across the tab 92 and secured via their respective fastening pairs 91, 91b. Once tabs 94 are in place, then tab 92 is secured to the outer surface 89 via its fastening pair 91, 91a.

The outer tabs 92a and 92b may then be secured in a similar manner. After securing tabs 92a and 92b, tab 92c may need adjustment, or tabs 94 as will be appreciated. This may be conveniently done once the tabs are initially secured. Care must be taken during the steps to ensure that one tab is not secured more tightly than another, or not sufficiently tight enough so that the scaffold 10 is permitted to recoil more in one area more than another, or to cause possibly dislodgment or loss of the scaffold-balloon dislodgment force due to uneven loads applied by the secured tabs 92, 94. The fasteners 91, 91b may correspond to an adhesive and suitable mating surface, respectively, for mating with the adhesive. The adhesive is exposed by removing a covering film just before a tab is being secured.

It will be appreciated that fastener 91, 91b pairs may not be needed. Instead, a removable tape may be pressed across a tab and adjacent outer surface 89 portion to hold the tab in place. This embodiment would share similarities to the embodiment depicted in FIGS. 8A-8C which uses a tape 82 to hold the end 80a in place to the outer surface 85.

Referring to FIG. 10C, the sheath 90 is shown secured to the medical device 18. In this configuration the medical device 18 and removable sheath 90 portion would be placed within the medical device packaging, sterilized and sent to the medical professional. The medical professional removes the medical device from the package, and then may remove the sheath 90 from the medical device 18 in the following manner. First, end 97c is pulled in the manner shown, thereby releasing tab from the outer surface 89 (or the tape covering this tab is removed). Then, ends 98a, 98b may be pulled with ends 97b, 97a in the following manner. With one hand end 97b is pulled to the right while end 98a is pulled to the left with the other hand. Then, after these tabs are released, end 98b is pulled to the left with one hand while end 97a is pulled to the right with the other hand. By performing this simultaneous removal, there is reduced risk of a tab when being removed imposing a torque or longitudinal force on the scaffold risking dislodgment or loss of dislodgment force.

Ends 97,98 may include indicia or guides for a user so that he/she is easily guided to removal of the sheath 90 in the manner just described. For example, the user may be instructed to remove tabs according to the color of the end. Suppose the tab ends are colored as follows: tab 97c is blue, tabs 97b and 98a are red and tabs 97a and 98b are green. Then, on the package for the medical device the following removal instructions for the sheath 90 may be provided, with reference to FIG. 10C, Step 1: arrange the medical device 18 so that the distal end 16 is nearest and the colored tabs face upwards.
Step 2: grip and pull the blue tab to the right (P2).
Step 3: grip the red tabs with the left and right hands.
Step 4: pull the one red tab to the left (P1) and the other to the right (P2).
Step 5: grip the green tabs with the left and right hands.
Step 6: pull the one green tab to the left (P1) and the other to the right (P2).

Figure 10D:
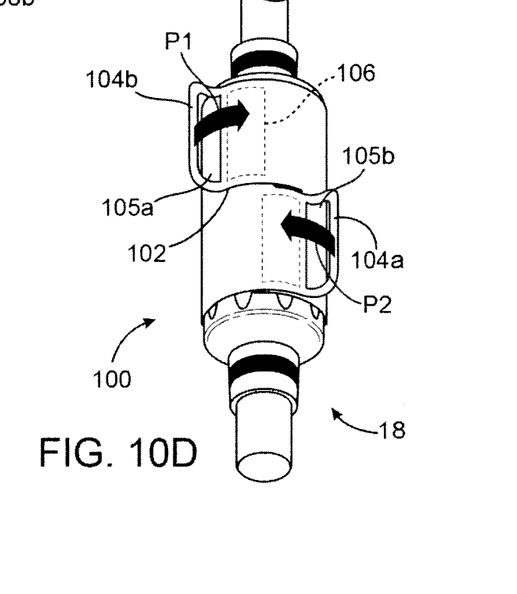

Referring to an additional aspect of the removable sheath disclosure, FIG. 10D depicts a sheath 100 disposed over the medical device 18. The sheath 100 may be constructed in the same manner and sharing the same features as sheath 90, except that sheath 100 has the following differences. Sheath 100 has only a single tab 102, 104 on each side of the sheath, rather than the two and three depicted for sheath 90.

Tabs 102 and 104 each have a semicircular pull tab 104a, 104b that is predisposed to extend up or curl up from the outer surface of the sheath. The adhesive fasteners 106 may alternatively be replaced by a first strip of tape wrapped about the circumference partially to secure tab 102 to the outer surface, and a second strip of tape wrapped about the circumference to secure tab 104 to the outer surface.

Each tab has a first and second colored portion 105a, 105b or alternatively (when tape is used) the tape extending over tab 104 has the second color and the tape extending over the tab 102 has the first color. Referring to the embodiment depicted in FIG. 10D, suppose the first color portion 105a is red and the second color portion 105b is green. Then, on the package for the medical device the following removal instructions for the sheath 100 may be provided, with reference to FIG. 10D, Step 1: arrange the medical device 18 so that the distal end 16 is nearest and the colored tabs face upwards.
Step 2: grip the green tab using the right hand.
Step 3: grip the red tab using the left hand.
Step 4: pull the green tab to the right (P2) while simultaneously pulling the red tab to the left (P1)

Figure 9A:
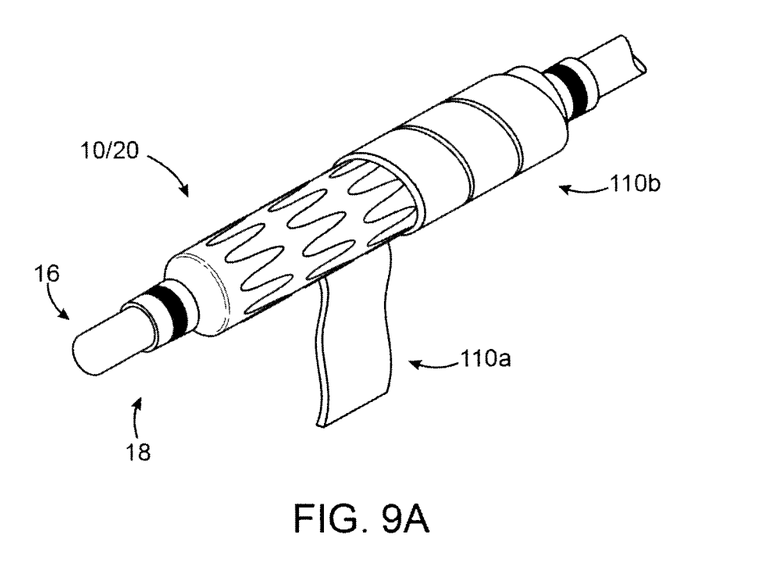
FIGS. 9A-9B illustrates aspects of a removable sheath according to a fifth embodiment.
Figure 9B:
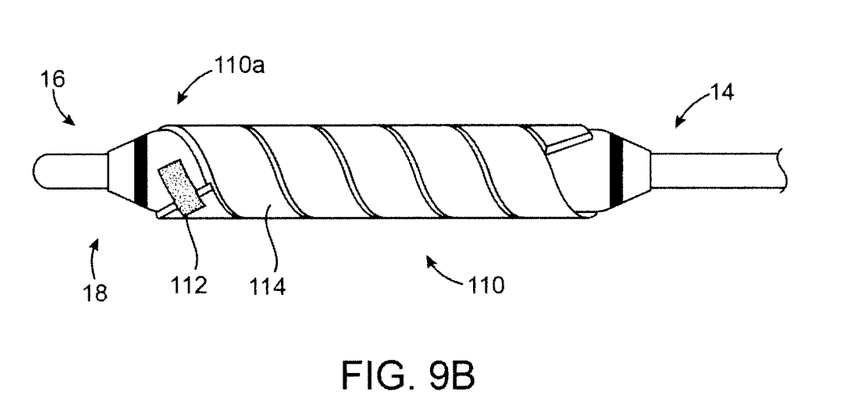

FIGS. 9A-9B show a sheath 110 according to a fifth aspect of the removable sheath disclosure. Sheath 110 is formed from a wrapping or strip of elastic material. Materials suitable for a sheath of this type may be the same type as those for sheath 80. Sheath 110 is configured for being wrapped about the crimped scaffold 10 in a helical fashion and then secured using a tape. An end 110b located nearest the proximal balloon marker is held and sheath 110 wrapped about the scaffold 10 as indicated by FIG. 9A.

Referring to FIG. 9B, the sheath 110 is secured to the scaffold 10 (hidden from view). As can be seen, the wrapping pattern is helical along the length of the medical device distal portion. The end 110a is secured to the outer surface 114 with a tape 112.

Preferably, the sheath 110 should have a width so that no more than 2, 3, or 4 wrappings about the circumference of the scaffold 10 are needed to cover the length shown in FIG. 9B. This is because when there are several wrappings required, i.e., the sheath width is narrow, there is more likely to result an uneven radial preload on the scaffold 10. For example, if several wrappings are required, it becomes more likely that the preload at the distal end is less than the proximal end where the wrapping was initiated.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for crimping, comprising:

using a scaffold having a scaffold diameter, the scaffold being made from a polymer tube and having a plurality of rings interconnected by links;

using a balloon catheter;

using a sheath having a sheath diameter, the sheath being configurable between an un-deformed state and a deformed state by radially stretching the sheath along its entire circumference, wherein the sheath is a tube having an undeformed diameter (d0) and when radially stretched the sheath has a deformed diameter (d3) at both ends thereof, and d3>d0;

crimping the scaffold to the balloon catheter including reducing the scaffold diameter from a first diameter (d1) to a second diameter (d2) by plastic deformation of the scaffold, wherein a ratio d1/d2 is at least 2.5; and reducing recoil effects in the crimped scaffold, comprising steps of deforming the sheath, including configuring the sheath into its deformed state to enable the sheath to receive the crimped scaffold, wherein d3>d2, receiving the crimped scaffold within the sheath configured in the deformed state, and after the crimped scaffold is received within the sheath configured in the deformed state, allowing the sheath to return to substantially the un-deformed state and attach to a surface of the scaffold rings;

wherein the sheath is configured for being manually removed from the scaffold before the scaffold is placed within a body.

2. The method of claim 1, wherein the ratio d1/d2 is greater than 3 or between 3 and 4.

3. The method of claim 1, wherein the step of reducing recoil effects further includes a step of maintaining the sheath in the deformed state using a supporting member having a bore, the receiving the crimped scaffold within the sheath step includes receiving the crimped scaffold within both the sheath and the supporting member bore, and the step of allowing the sheath to return to substantially the un-deformed state includes a step of removing the supporting member from the sheath or removing the sheath from the supporting member.

4. The method of claim 3, wherein the supporting member is a first and a second collet, each of which having a bore and supporting, respectively, a first and a second end of the sheath.

5. The method of claim 3, wherein the supporting member is a tube.

6. The method of claim 3, wherein the sheath has ends and a v-shaped cut is present at one or both of the ends.

7. The method of claim 1, further comprising a step of forming a weakened area on the sheath after the sheath is allowed to return to substantially the un-deformed state.

8. A method for crimping, comprising:

using a scaffold having a scaffold diameter, the scaffold being made from a polymer tube and having a plurality of rings formed by struts connected at crowns;

using a balloon catheter;

using a tubular sheath having ends, a sheath diameter and a v-shaped cut is present at one or both of the ends;

crimping the scaffold to the balloon catheter including reducing the scaffold diameter from a first diameter (d1) to a second diameter (d2) by plastic deformation of the scaffold, wherein a ratio d1/d2 is at least 2.5; and reducing recoil effects in the crimped scaffold, comprising steps of radially stretching the sheath along its entire circumference to increase the sheath diameter from an undeformed diameter (d0) to a deformed diameter (d3) at both of its ends, wherein d0 is less than d2 and d3 is greater than d2, receiving the crimped scaffold within the radially stretched sheath, and after the crimped scaffold is received within the radially stretched sheath, allowing the radially stretched sheath to return to a substantially un-deformed state, thereby attaching to surfaces of the scaffold struts;

wherein the sheath is configured for being manually removed from the scaffold before the scaffold is placed within a body.

9. The method of claim 8, wherein the step of reducing recoil effects in the crimped scaffold step includes a step of supporting the radially stretched sheath on a support member while the crimped scaffold is received within the radially stretched sheath.

10. The method of claim 9, wherein the supporting member is a first and a second collet, each of which having a bore and supporting, respectively, first and second ends of the radially stretched sheath.

11. The method of claim 9, wherein the supporting member is a tube.

* * * * *